US009959697B2

(12) United States Patent
King et al.

(10) Patent No.: US 9,959,697 B2
(45) Date of Patent: May 1, 2018

(54) LABORATORY CONTAINER TRANSFER DEVICE

(71) Applicant: THERMO ELECTRON MANUFACTURING LIMITED, Altrincham (GB)

(72) Inventors: Brian King, Runcorn (GB); Harald Ritchie, Chester (GB)

(73) Assignee: Thermo Electron Manufacturing Limited, Altrincham (GB)

( * ) Notice: Subject to any disclaimer, the term of this patent is extended or adjusted under 35 U.S.C. 154(b) by 0 days. days.

(21) Appl. No.: 14/470,638

(22) Filed: Aug. 27, 2014

(65) Prior Publication Data
US 2015/0063956 A1 Mar. 5, 2015

(30) Foreign Application Priority Data
Aug. 30, 2013 (GB) .................... 1315498.4

(51) Int. Cl.
*G07F 11/54* (2006.01)
*G07F 11/24* (2006.01)
*G07F 17/00* (2006.01)
*G01N 35/04* (2006.01)
*B65G 47/84* (2006.01)

(52) U.S. Cl.
CPC ............ *G07F 11/54* (2013.01); *G01N 35/04* (2013.01); *G07F 11/24* (2013.01); *G07F 17/0092* (2013.01); *B65G 47/846* (2013.01); *G01N 2035/0439* (2013.01); *G01N 2035/0465* (2013.01)

(58) Field of Classification Search
CPC ............ G01N 2035/0465; G01N 2035/0439
See application file for complete search history.

(56) References Cited

U.S. PATENT DOCUMENTS

| 4,595,562 | A |   | 6/1986  | Liston et al. |              |
|-----------|---|---|---------|---------------|--------------|
| 4,830,171 | A | * | 5/1989  | Kupper        | B65H 67/068  |
|           |   |   |         |               | 198/320      |
| 5,250,440 | A | * | 10/1993 | Kelln         | G01N 35/025  |
|           |   |   |         |               | 356/246      |
| 5,682,026 | A | * | 10/1997 | Auclair       | G01N 35/04   |
|           |   |   |         |               | 235/375      |
| 5,860,563 | A | * | 1/1999  | Guerra        | B65G 47/24   |
|           |   |   |         |               | 221/172      |

(Continued)

FOREIGN PATENT DOCUMENTS

| CA | 2254017 | 5/2000  |
|----|---------|---------|
| EP | 0126636 | 11/1984 |

(Continued)

*Primary Examiner* — P. Kathryn Wright

(57) ABSTRACT

A laboratory vial transfer device for automatically transferring laboratory vials from a transport package containing a plurality of said vials, comprising: a vial feeder configured to connect to the transport package after the package has been opened, so as to feed vials directly from the package without manual contact, wherein the vial feeder comprises a rotatable carousel having a plurality of vial receiving positions located on the carousel each for receiving a single vial and adapted to collect the vials from the opened package into respective vial receiving positions upon operation of the carousel, wherein the carousel is operable to feed the vials from their respective vial receiving positions to an exit position.

16 Claims, 13 Drawing Sheets

(56) References Cited

U.S. PATENT DOCUMENTS

| | | | |
|---|---|---|---|
| 6,082,582 A * | 7/2000 | Chiou | B23Q 7/001 221/168 |
| 6,551,833 B1 * | 4/2003 | Lehtinen | G01N 35/04 198/349.5 |
| 2002/0001542 A1 | 1/2002 | Itoh | |
| 2009/0254214 A1 | 10/2009 | Kudera et al. | |
| 2013/0236276 A1 * | 9/2013 | Richter | B01L 3/00 414/222.07 |

FOREIGN PATENT DOCUMENTS

| | | |
|---|---|---|
| JP | 7206140 | 8/1995 |
| WO | 9858765 | 12/1998 |
| WO | 2013059568 A1 | 4/2013 |

* cited by examiner

LABORATORY CONTAINER TRANSFER DEVICE

CROSS REFERENCE TO RELATED APPLICATIONS

This application claims the priority benefit under 35 U.S.C. § 119 to Great Britain Patent Application No. 1315498.4 by Brian King and Harald Ritchie for "Laboratory Container Transfer Device," filed on Aug. 30, 2013, the disclosure of which is incorporated herein by reference.

FIELD OF THE INVENTION

The present invention relates to the automated handling of laboratory containers, for example vials.

BACKGROUND

The transfer of containers such as sample vials from their transport packaging to the laboratory workbench, workspace or an autosampler for example has conventionally been a completely manual process. Such manual handling is slow, inefficient and presents a potential source of sample contamination.

Automated systems for handling vials are known in industrial settings, such as in the pharmaceutical industry, in which a large hopper is filled with sometimes hundreds of vials that can be dispensed from the hopper to a downstream processing operation. However, such systems are designed for very large scale use and are not suitable for medium or low throughput use in transferring vials, perhaps one vial at a time, out of their small transport package to the laboratory workbench, workspace or an autosampler.

In US 2009/0254214 A is disclosed a vial dispensing system, designed for use with, for example, a medicament dispensing system, that accepts vials into a spiral delivery chute while a platter positioned below the chute is rotated in one direction to move the vials along the chute for loading. When the platter is rotated in the counter direction loaded vials may be dispensed from the chute for pick up by a vial transporting system. However, vials must still be manually handled to load them individually into the delivery chute, which is inefficient and potentially contaminates them.

SUMMARY

According to an aspect of the present invention there is provided a laboratory vial transfer device for automatically transferring laboratory vials from a transport package containing a plurality of said vials, comprising: a vial feeder configured to connect to the transport package after the package has been opened, so as to feed vials directly from the package without manual contact, wherein the vial feeder comprises a rotatable carousel having a plurality of vial receiving positions located on the carousel each for receiving a single vial and adapted to collect the vials from the opened package into respective vial receiving positions upon operation of the carousel, wherein the carousel is operable to feed the vials from their respective vial receiving positions to an exit position.

According to another aspect of the present invention there is provided a method of automatically transferring laboratory vials from a transport package containing a plurality of said vials, comprising: opening the package to provide an open end of the package; connecting the open end to a vial feeder configured to connect to the transport package after the package has been opened, the vial feeder comprising a rotatable carousel having a plurality of vial receiving positions located on the carousel each for receiving a single vial and adapted to collect the vials from the opened package into respective vial receiving positions upon operation of the carousel; operating the carousel to feed vials directly from the package without manual contact, whereby the carousel feeds the vials from their respective vial receiving positions to an exit position.

According to yet another aspect of the present invention there is provided a laboratory container transfer device for automatically transferring laboratory containers from a package containing a plurality of said laboratory containers, comprising: a container feeder configured to connect to an array of laboratory containers from the package, so as to feed containers directly from the array without manual contact.

The package containing the plurality of laboratory containers preferably contains the laboratory containers arranged in an array, e.g. an ordered (non-random) arrangement. The array of laboratory containers is most preferably the array in the package and thus preferably the container feeder is configured to connect to the package containing the plurality of laboratory containers after the package has been opened.

According to still another aspect of the present invention there is provided a laboratory container transfer device for automatically transferring laboratory containers from a package containing a plurality of said laboratory containers, comprising: a container feeder configured to connect to the package containing the plurality of laboratory containers after the package has been opened, so as to directly feed containers directly from the package without manual contact.

The container feeder preferably comprises a conveyor having a plurality of container receiving positions located on the conveyor each for receiving a single laboratory container and adapted to collect the laboratory containers from the array (e.g. opened package) into respective container receiving positions upon operation of the conveyor, wherein the conveyor is operable to feed the laboratory containers from their respective container receiving positions to an exit position, i.e. from where they exit from the conveyor. Thereafter, the containers may be transferred to a receiver for further processing.

It is an advantage of the invention that the laboratory containers can be transferred directly and automatically from a bulk transport package to a feeder and then dispensed to a receiver, for example, to a robotic system (e.g. autosampler or robotic handling system), receptacle (e.g. tray or rack) or processing device (e.g. printer or liquid dispensing unit) without any manual (i.e. by human hand) contact. This lack of manual handling eliminates a potential source of contamination. The user needs only to open the package and connect the opened package to the feeder but does not need to touch any of the containers inside the package. Thus, the device is an automated laboratory container transfer device for mechanically transferring containers from a transport package. The containers are preferably aligned in the package in an array so that in this way individual, correctly aligned laboratory containers are fed into a collection feeder for transfer to a receiver. In addition to the advantages of reducing manual intervention and maintaining cleanliness the invention also facilitates a reduction in breakages and handling errors, a reduction in container wastage and an integration of workflow as the containers can be fed directly to a further processing device.

When the package is empty of containers, the package may be disconnected from the feeder, e.g. to be discarded. The feeder may then be connected to a fresh package containing a plurality of containers.

The container feeder preferably connects directly to the package so that the laboratory containers therein do not need to be first removed from the package in order to be fed to the feeder. In other words, the containers are fed directly from their package to the feeder. Thus, the device eliminates a separate step for the user of removing the containers from the package. In another embodiment, a plurality of laboratory containers may be transferred as an array from the package into a carrier that connects to the feeder, thus allowing the feeder to feed laboratory containers from the array in the carrier albeit the containers have been removed from the package.

The container feeder may have a recess or receiving space in which at least a portion, preferably at least an end, of the package (the open end), optionally substantially the whole package, may be received, preferably in a close fitting manner, thereby to connect to the package. In a preferred embodiment, the package is a rectangular cuboid and the container feeder has a rectangular receiving space to receive at least an end of the package in a close fitting manner. A detachable carrier, as described in more detail below, may also be provided that has a receiving space for receiving at least a portion of the package, optionally substantially the whole package, preferably in a close fitting manner. Additionally or alternatively, the detachable carrier may contain the array of containers, e.g. after they have been transferred to the carrier from the package.

The container feeder may connect to the package by clipping or otherwise attaching to the package. Thus, the container feeder preferably has one or more fasteners, e.g. clips, to attach the package. Resilient fasteners are preferred. The package preferably has a one or more recesses to receive the one or more fasteners. Alternatively or additionally, in a preferred embodiment, the device may further comprise a carrier into which is inserted the package (or into which is transferred the array of containers from the package) and the container feeder may attach to the carrier to thereby more securely connect to the package (after the package has been opened). Thus, the container may have one or more fasteners, e.g. clips, to attach to the carrier. The container feeder may attach to the carrier by clipping or otherwise attaching to it. In a preferred embodiment, the carrier has one or more fasteners, e.g. clips, to attach to the container feeder. Once again, resilient fasteners are preferred. The container feeder may clip or otherwise attach to both the package and the carrier. The carrier is preferably detachable from the feeder for insertion of the package into the carrier, and for removal of the package from the carrier when the package is empty, and attachable to the feeder once the carrier is loaded with the package containing the plurality of containers.

The laboratory containers may be, for example, vials, especially glass sample vials, test tubes, bottles, flasks, nuclear magnetic resonance (NMR) tubes, solid phase extraction (SPE) tubes etc. Typically, the containers are vials. However, it will be appreciated that the foregoing list of containers is not limiting on the scope of the invention. The laboratory containers generally may be any vessel for containing a liquid or solid, especially a liquid, laboratory sample. The laboratory samples are typically designed to be analysed by one or more laboratory analytical techniques. Autosampler vials, e.g. for chromatography, or other chromatography vials, which are typically made of glass, are a preferred type of container for which the invention is suitable. The dimensions of the containers are not a limiting factor and the invention could be used with a wide range of container sizes with appropriate scaling of the device components. The material of which the containers are made is not limited and may be, for example, glass or plastic, although glass is preferred.

The package containing the plurality of said laboratory containers is preferably the package in which the containers are transported from a manufacturer or supplier to a customer or end user, i.e. it is preferably a transport, i.e. delivery package. The transfer device of the invention is thus designed to be used by a customer or end user. The package is typically a box and is usually a rectangular cuboid box. The box may be made of cardboard or other conventional package material. The containers are preferably packed and aligned in the package.

The package of containers is desirably configured to fit and connect to the container feeder. This allows the package to be placed complete, full of containers, into an operable position with the feeder, which allows the containers to be extracted singly from the package into the feeder.

When the package is opened, for example by the user, it thereby presents an opening or open end. The package may then be connected to the container feeder with the open end adjacent the feeder. The containers are fed through the opening or open end of the package into the respective container receiving positions of the conveyor as the conveyor moves.

The package is designed to be held vertically in use when connected to the feeder. The package is designed to be held upturned (i.e. open end down) with the feeder positioned below the package to receive containers from the open package under gravity. That is, the feeder is preferably gravity fed with containers from the package.

The conveyor is preferably adapted to collect the laboratory containers one at a time (singly) from the connected opened package into respective container receiving positions on the conveyor. Moreover, the conveyor is preferably designed to deliver the laboratory containers one at a time from their respective container receiving positions to the exit or receiver.

The conveyor is preferably a rotatable carousel, i.e. a circular conveyor that is rotatable. A carousel can be a compact and robust conveyor and may be constructed as a solid component with cut out portions in its (circular) outer edge that form the container receiving positions.

Thus, the container feeder preferably comprises a rotatable carousel having a plurality of container receiving positions located on the carousel each for receiving a single laboratory container and adapted to collect the laboratory containers from the opened package into respective container receiving positions upon rotation of the carousel. The rotatable carousel is rotatable to feed the laboratory containers from their respective container receiving positions to an exit or receiver.

The carousel is preferably designed to not only collect the laboratory containers one at a time from the package or carrier into respective container receiving positions on the carousel but feed the laboratory containers one at a time from their respective container receiving positions to the exit or receiver.

The feeder, in particular the conveyor or carousel thereof, is preferably connected in use to a drive for operating (rotating) the conveyor or carousel, which could be a manually operated drive but is preferably a motorised drive. The drive is preferably controlled by a controller, more preferably an electronic controller. The controller may include a computer. The drive may be part of a base unit for positioning on a bench top for instance. The feeder preferably is a detachable part that connects to the base unit. The feeder can be disconnected from the drive (e.g. by detaching the feeder from the base unit), for example when it is required to unload the feeder and/or connect the feeder to a fresh package containing the laboratory containers. The feeder can then be reconnected to the drive (and base unit), for instance when it is required to operate the feeder to deliver containers from the package.

Other preferred features of the invention include one or more of: a lock on the conveyor (carousel) to prevent accidental operation (rotation) of the conveyor (carousel), especially when it is disconnected from a drive on a base unit, e.g. a spring loaded lock; a switch to check for empty container receiving positions in the conveyor or carousel, especially as it rotates; and a position encoder to detect the position of the conveyor or carousel as it moves or rotates, e.g. a rotary encoder.

A robotic system is preferably provided, for example on the mentioned base unit, for transferring containers to a receiver after they have left the exit of the feeder. Alternatively, the containers may be fed from the feeder exit directly to the receiver. The device is thereby able to transfer the containers singly to any of the robotic systems, receptacles or processing devices in the following non-exhaustive list, which are examples of receivers:

1. An autosampler rack
2. A compound storage rack
3. A compound storage rack
4. A crimper assembly unit
5. A screw closure unit
6. A printer unit
7. A label assembly applicator
8. A liquid dispensing unit
9. A weighing unit,
10. A tare weighing unit
11. A heating unit
12. A barcode reader Any of the above, that is to say any of the robotic system, receptacle or processing devices, can be connected to the base unit that the feeder connects to, so that they are integrated into its operation or the transfer device may be used to populate transport trays, which may then be moved e.g. by a robotic arm or autosampler unit.

Other features and advantages of the present invention will be apparent from the following detailed description of embodiments and the accompanying drawings.

The invention may be put into practice in a number of ways, some of which will now be described by way of example only and with reference to the accompanying drawings.

DETAILED DESCRIPTION OF SPECIFIC EMBODIMENTS

Figure 1A:
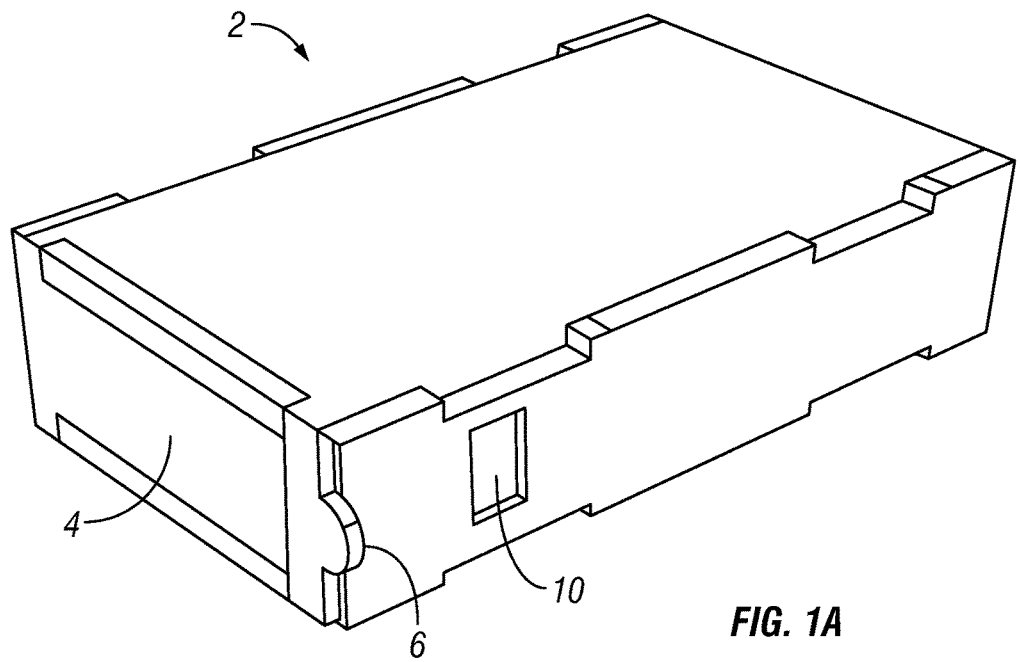
FIGS. 1A, 1B, and 1C show an embodiment of a package containing vials in a sealed state (FIG. 1A), partially open state (FIG. 1B) and open state (FIG. 1C).

Referring to FIG. 1A there is shown a package 2 containing a plurality of vials inside. A standard package size contains 96 vials for example. The package is used to transport the vials from the manufacturer or supplier to the end user in the laboratory. The package is made of a conventional low cost material and is constructed from a cut and fold assembly. The package is generally a rectangular cuboid box with an openable cover 4 at one end. The cover 4 is sealed for transit with a clip 6 on the cover that fastens to one side of the package. For transit the whole package may be protected against ingress of dust by a removable thin transparent film.

Figure 1B:
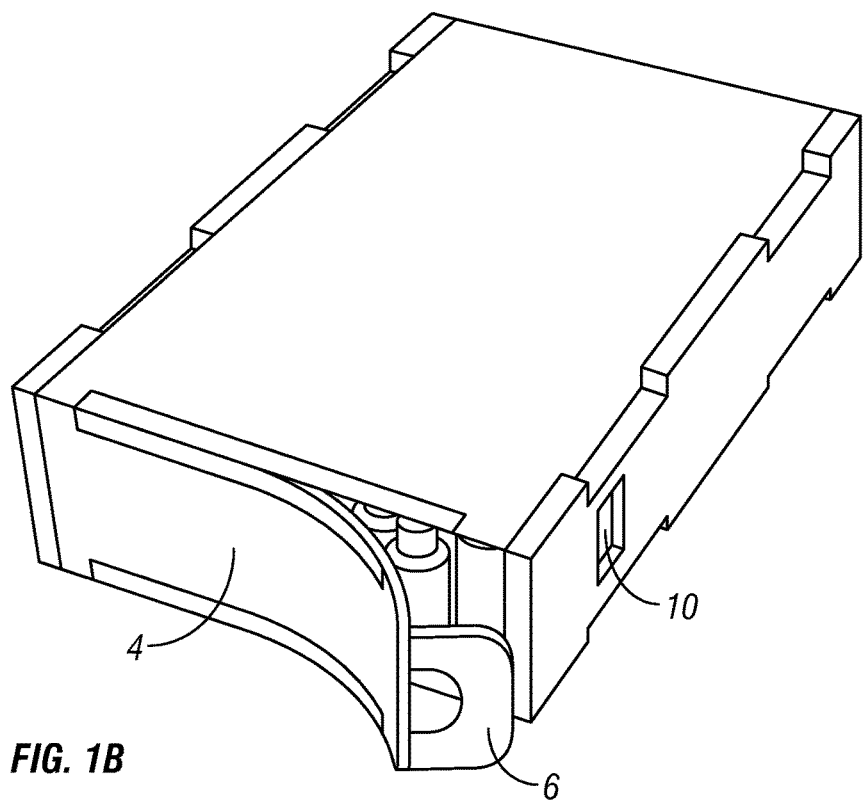
Figure 1C:
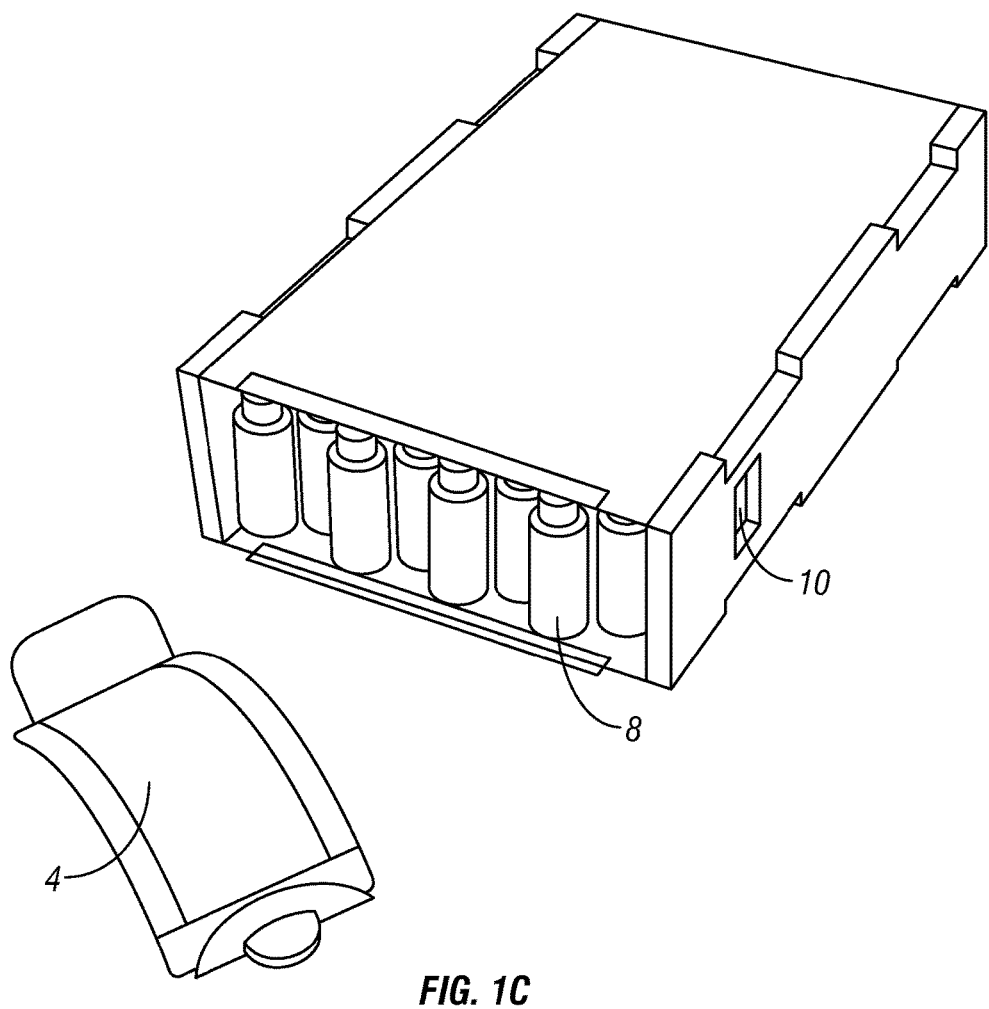

When the vials are required to be used, the transparent film is first removed and then the cover 4 is opened by unfastening the clip 6 and peeling back the cover as shown in FIG. 1B. FIG. 1C shows the cover 4 completely removed with the uniformly packed and aligned vials 8 inside visible through the open end. The package further comprises a recess 10 on one side proximate to the open end and an identical recess on the opposite side (not visible). The purpose of this recess will be made clear in the following description.

Figure 2:
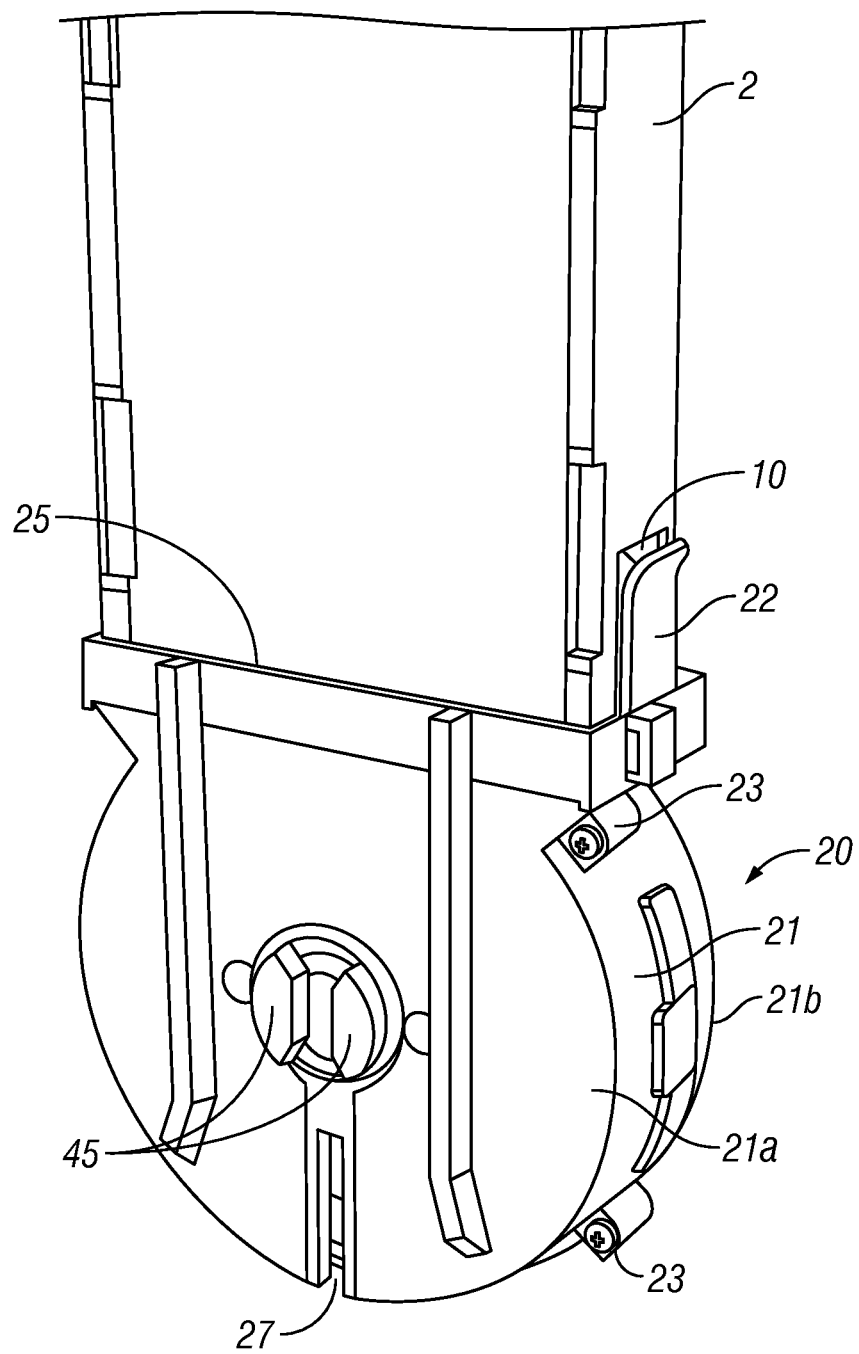
FIG. 2 shows an arrangement wherein the opened package is connected to a container feeder in accordance with the invention.

Referring to FIG. 2, the package 2 shown in FIG. 1 is dimensioned to connect to a container feeder 20. The feeder will be described in more detailed below. The feeder 20 comprises a casing 21, which comprises two halves 21a and 21b which are secured together, e.g. using screws 23 shown. The casing 21 of the feeder carries two resilient clips 22 (only one of which is visible in FIG. 2) that fit into the respective recesses 10 on the package to thereby fasten the package in place on the feeder. The feeder 20 also has a receiving space in the form of recess 25 in its top that is dimensioned and shaped (rectangular) to receive the open end of the package 2 in a close fitting manner. The open end of the package 2 shown in FIG. 1C is therefore the end connected to the feeder 20. In this way, vials may be collected by the feeder from the package as hereafter described. FIG. 2 shows the orientation of the feeder 20 and package 2 in use, i.e. with the package upturned so that its open end is downwards and the feeder is positioned underneath the package (underneath the open end thereof) for gravity feeding of vials from the package. It will be appreciated that the package will normally be positioned with its cover at the top during removal of the cover (so that any vials do not fall out of the opened package) and only once the feeder is connected to package will the package be inverted to the position shown in FIG. 2.

Figure 3A:
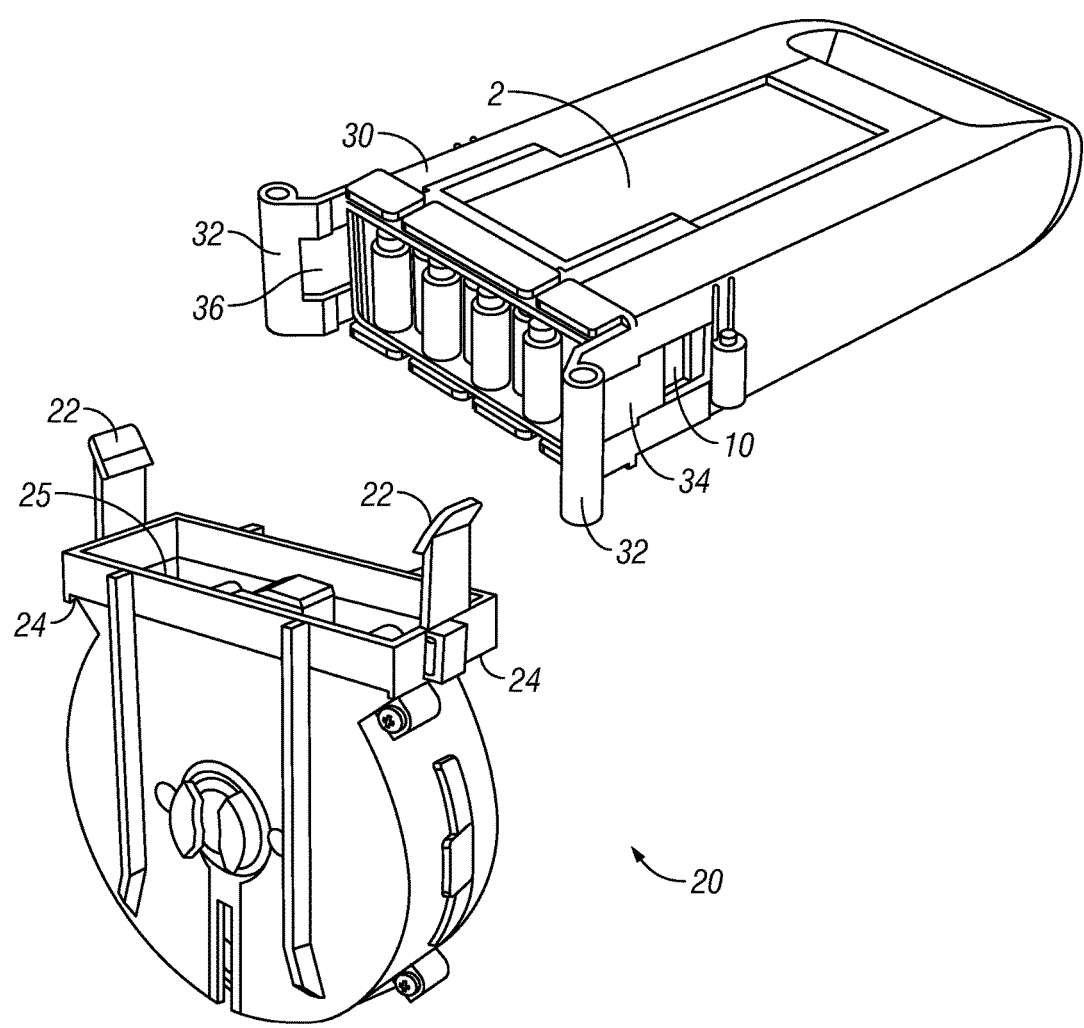
FIGS. 3A and 3B show an alternative arrangement in accordance with the invention wherein the package is inserted into a carrier, with the carrier shown detached from the container feeder in FIG. 3A and attached to the feeder in FIG. 3B.
Figure 3B:
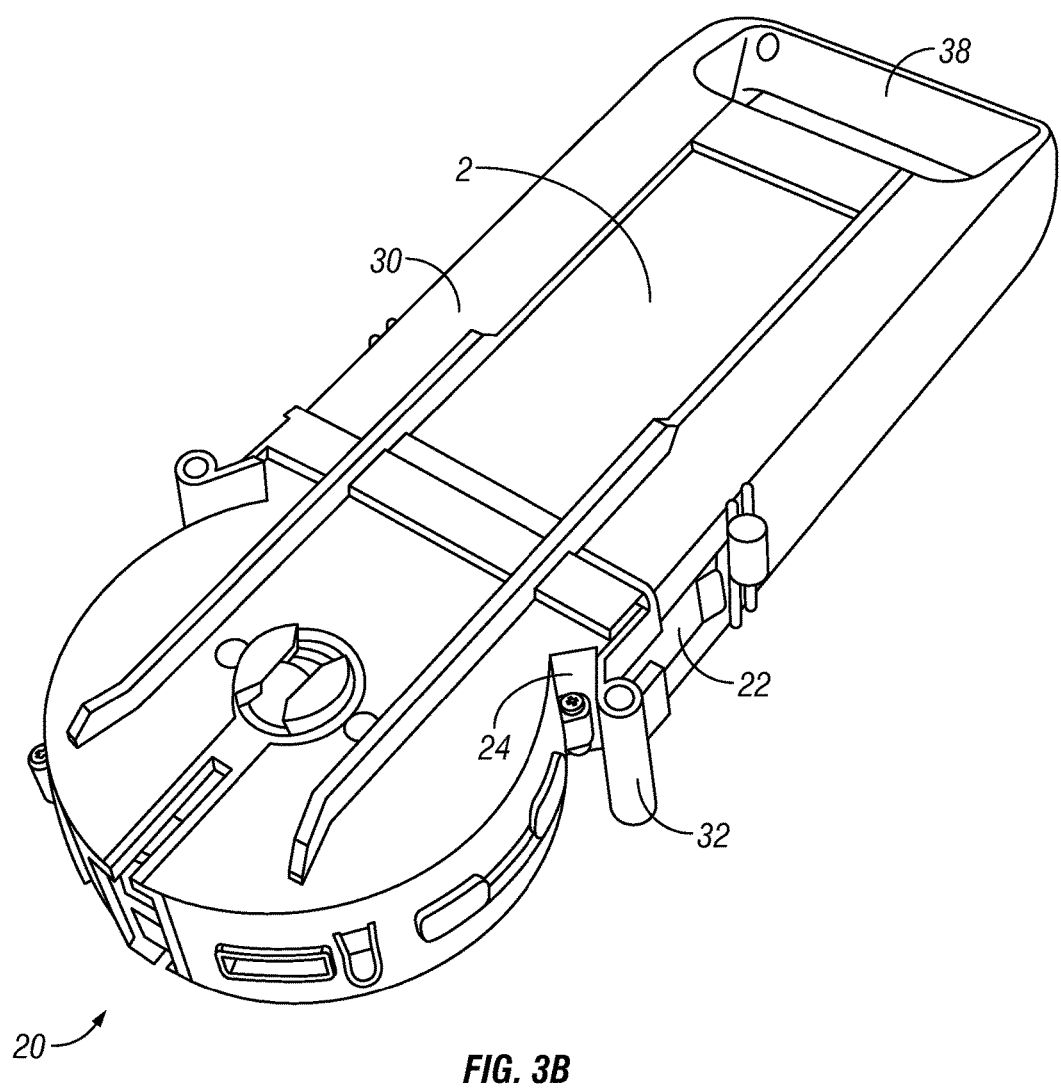

In an alternative arrangement shown in FIGS. 3A and 3B, the package 2 may be inserted into a carrier 30. The carrier is robust and provides support to the package as well as assists connection of the package to the feeder 20. This makes handling of the package easier and safer, especially during connection of the package to the feeder. The carrier may have a handle 38. The carrier 30 is preferably a rigid body, e.g. of plastic, with a recess or receiving space, in this case of rectangular shape, to accommodate the package. The open end of the package remains exposed when the package is inserted in the carrier. The carrier 30 also has resilient clips 32 which fasten over recess 24 on the container feeder 20 as shown in FIG. 3B. The clips 22 on the feeder 20 still fit into the recesses 10 in the package 2 as the carrier has cut out portions 34 on its sides to allow the package recesses 10 to be accessed. The clips 22 on the feeder pass through apertures 36 in the clips 32 of the carrier so that they can reach the recesses 10. In FIG. 3A, more visible is the receiving space 25 in the top of the feeder that is dimensioned and shaped to receive the open end of the package 2 with a close fit. The shape of the space 25 is rectangular to receive the rectangular cuboid shaped package.

Figure 4:
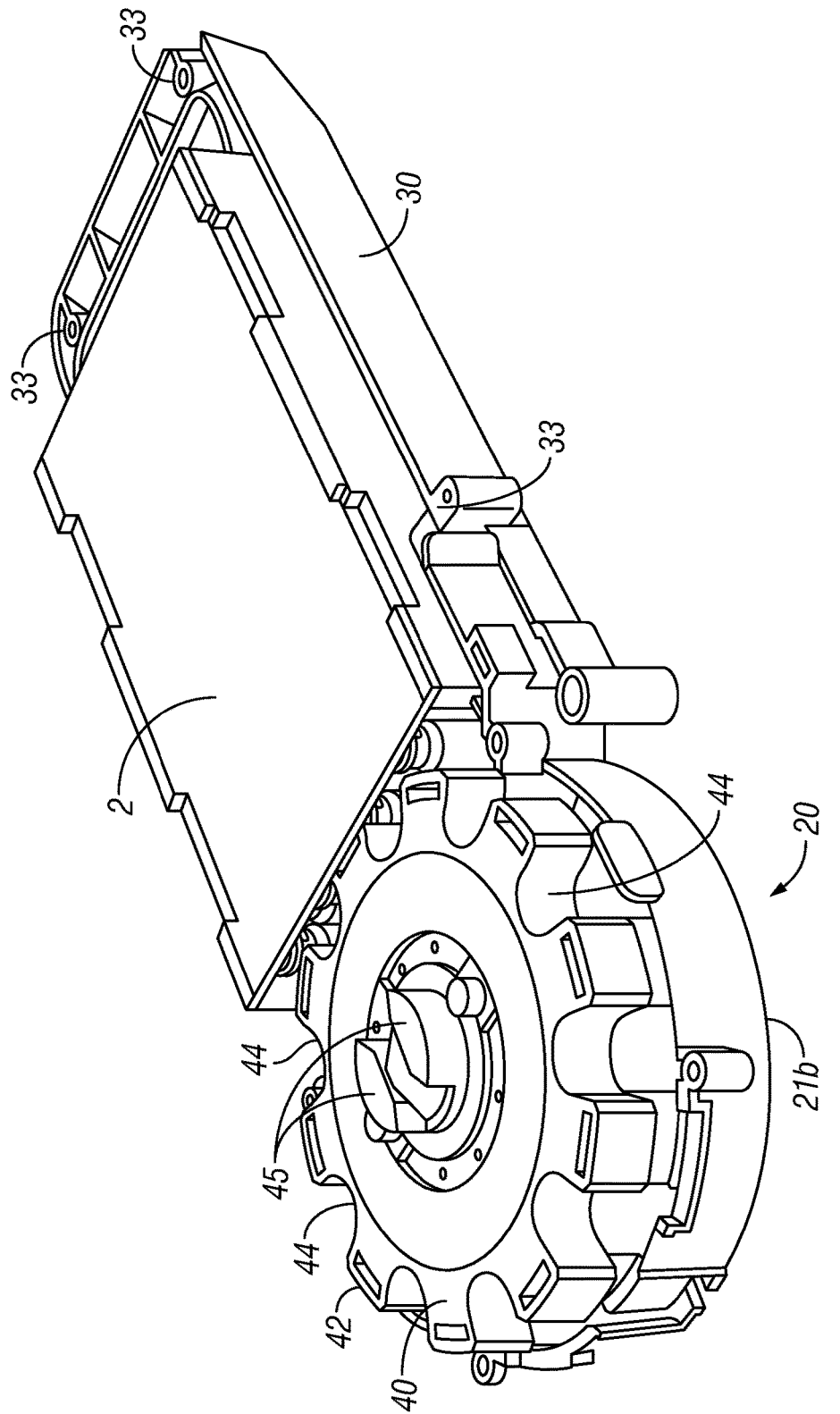
FIG. 4 shows a view of a container feeder connected with a package in its carrier in accordance with the invention, wherein the feeder and carrier are shown partially disassembled.

Referring to FIG. 4, there is shown a view of the connected container feeder 20 and package 2 in its carrier 30, wherein the feeder 20 and carrier 30 are shown partially disassembled in order to display internal features. The carrier 30 is made of two modular halves that fasten together, e.g. using screws that pass through screw holes 33 in each half. One of the modular halves of the carrier 30 has been removed in FIG. 4 and the other half is shown holding the package 2. The feeder 20 has had one half of the casing 21a removed (after removing the screws 23 shown in FIG. 2) so that casing half 21b remains. Inside the casing 21 of the feeder is a rotatable carousel 40 that comprises in its outer edge 42 a plurality of cut out portions 44 (three of which are indicated). The cut out portions 44 are equally spaced around the edge of the carousel. The cut out portions 44 are dimensioned so as to accommodate therein a vial from the package in each cut out portion. Thus, the carousel functions as a vial selector. Two lugs 45 projecting from the centre of the carousel 40 enable the carousel to be located in a base unit as hereafter described. The lugs 45 project through an aperture in the casing 21 of the feeder as shown in FIG. 2.

Figure 5:
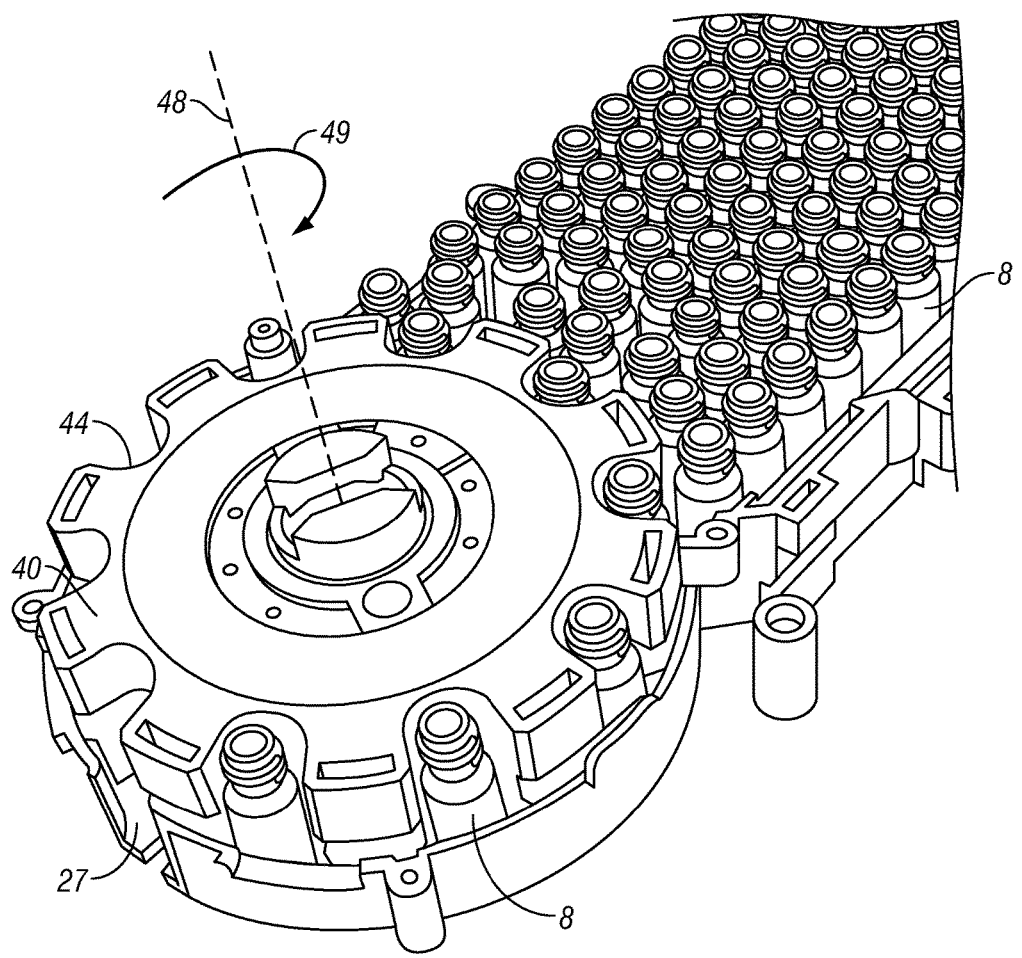
FIG. 5 shows a view similar to FIG. 4 but with the package in transparent form so that the plurality of vials inside is visible.

FIG. 5 shows the view of FIG. 4 but with package 2 in transparent form so that the array of vials 8 inside is visible. As the carousel 40 is rotated about an axis 48 in a direction indicated by arrow 49, the cut out portions 44 are thus rotated so that the vials 8 from the package are collected one at a time into each of the cut out portions 44 in the carousel as the cut out portions pass the open end of the package. As shown in FIG. 2, the vertically positioned and inverted opened package 2 causes vials to fed under gravity to the carousel. The vials 8, being held singly in respective cut out portions 44, are thereby fed around by the rotating carousel until each cut out portion reaches an exit of the feeder in the form of an aperture 27 in the casing 21 of the feeder. A switch may check for any empty cut out portions as the carousel rotates. The exit aperture 27 is located on the opposite side of the carousel to the open package. As shown in FIG. 2, the feeder and connected package are positioned vertically in use so that the exit 27 is located at the bottom of the feeder and thus each vial drops out of the exit aperture (under gravity) when it reaches it. The cut out portions left empty after their vials drop out of the exit aperture proceed as the carousel is rotated whereby eventually they pick up fresh vials from the package and the operation continues.

In an alternative embodiment not shown, the array of vials could be emptied from a package similar to package 2 into a carrier similar to carrier 30 without manual handling and then fed from the carrier into the feeder 20. For example, by removing one of the large faces of the package to expose the vials and placing them into contact with one half of the carrier the vials may be transferred as an array into the carrier. The other half of the carrier may then be placed on top of the first half to enclose the transferred vials in the carrier. With the carrier connected to the feeder, the vials may be directly fed from the contained array.

Figure 6:
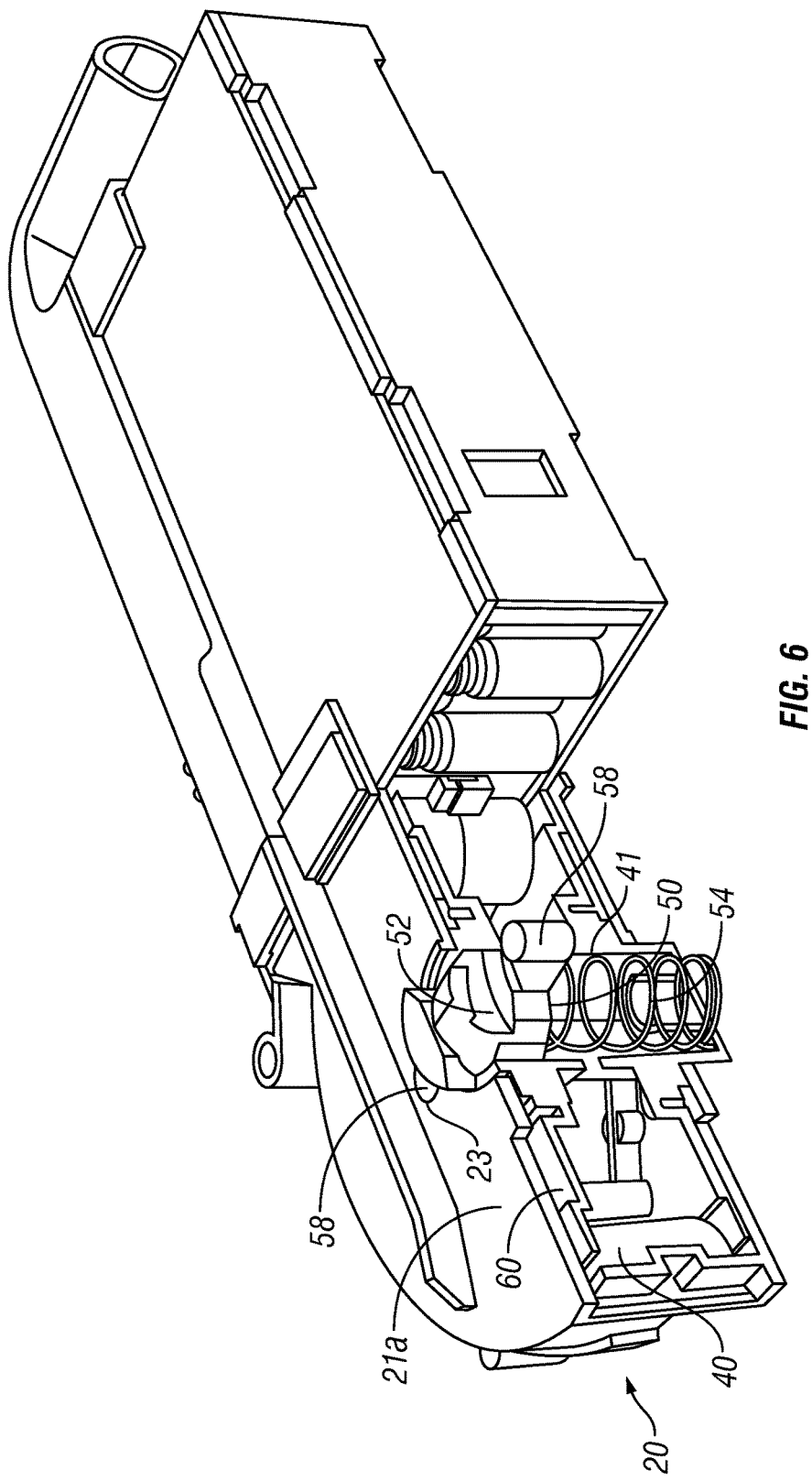
FIG. 6 shows a cut away view of the container feeder showing internal detail of a rotatable carousel inside the feeder for feeding vials, which has a lock to prevent accidental rotation of the carousel and a position encoder to determine the position of the carousel.

Referring to FIG. 6, there is shown a cut away view of the container feeder 20 showing internal detail of the carousel 40, which has a lock 50 to prevent accidental rotation of the carousel. The lock 50 is spring loaded. The lock comprises a centre piece 52 that moves slidably within a central bore 41 in the carousel 40. The centre piece 52 has two lugs 58 that project from it. The centre piece 52 of the lock is biased in the bore 41 of the carousel 40 by a spring 54 located in the bore. The spring 54 biases towards the lock so that the projecting lugs 58 engage apertures 23 in the casing 21 that surrounds the carousel, specifically in one side 21a of the casing. When the lock is biased in this way, the lugs engaged with casing 21 prevent rotation of the carousel. When the feeder 20 is removed from its operating position (i.e. when it is not located in its base unit as hereafter described), a user can press in the centre piece 52 of the lock thereby to disengage the lugs 58 from the apertures 23 in the casing 21 and manually rotate the carousel to empty, i.e. unload, any vials from the feeder if desired. When the feeder 20 is positioned in use as hereafter described, the lock will become pressed in so as to permit the carousel to be rotated by the drive. Also indicated in FIG. 6 is a position encoder 60 on the carousel to detect the rotational position of the carousel. The position may be input to a controller of the device (not shown). The controller may also control the drive and thus parameters such as the feeding speed (e.g. carousel rotational speed) of the device according to a user's set speed.

Figure 7:
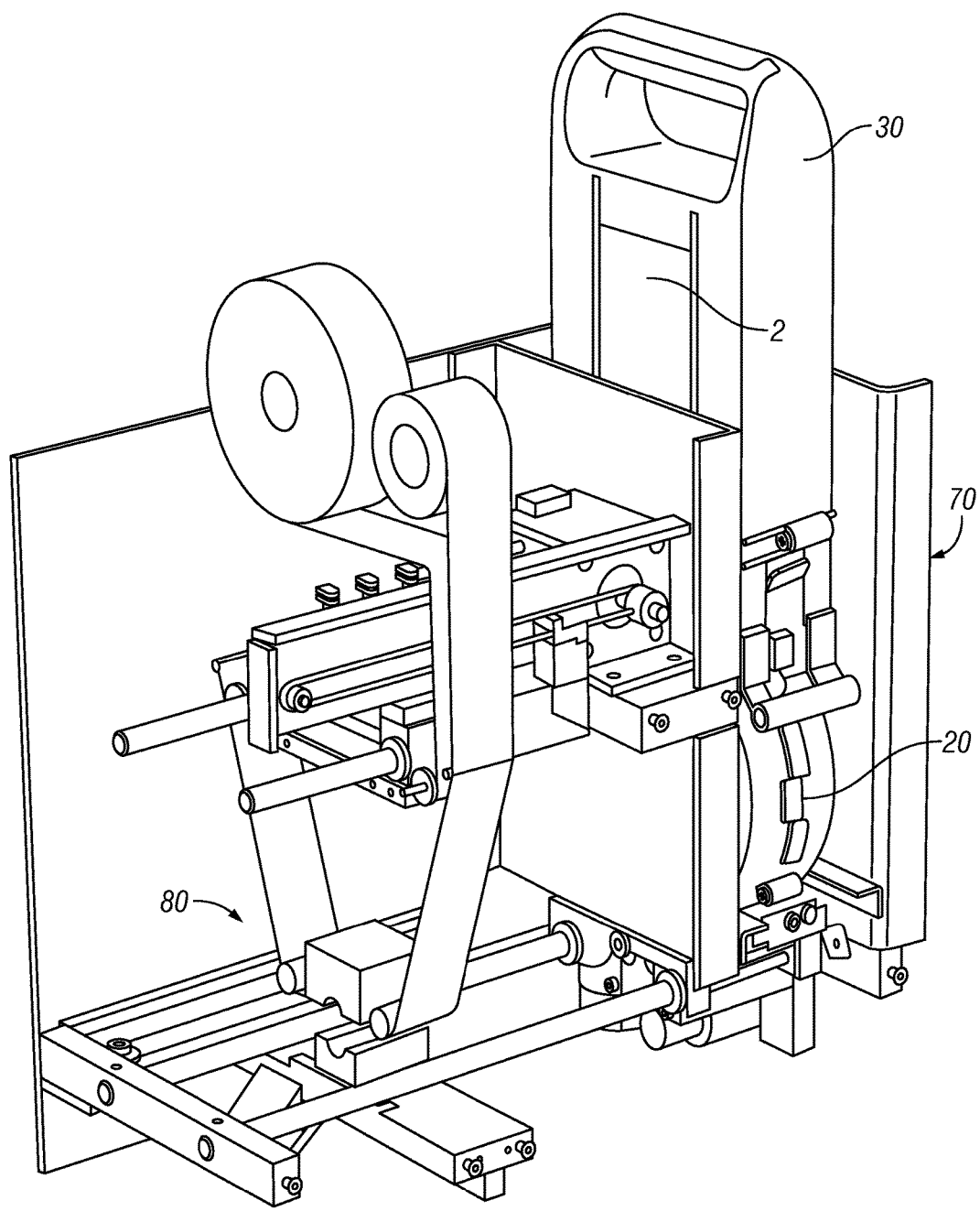
FIG. 7 shows an embodiment of an overall whole workflow in which a container feeder in accordance with the invention is shown in an operating position located in a base unit which in turn is interfaced to a printing unit.

FIG. 7 shows an embodiment of an overall whole workflow in which a container feeder 20 is connected with a package carrier 30 loaded with an opened package 2 in accordance with FIGS. 1 to 6. The container feeder 20 is mounted vertically (with inverted package 2 in its top) in an operating position on a base unit 70, which in turn is interfaced to a printing unit 80. The base unit 70 can be positioned for example on a bench top. The base unit comprises a drive (not shown) for operating (i.e. rotating) the carousel 40 of the feeder 20, which could be a manually operated drive but is in this preferred example a motorised drive. With the feeder connected to the drive on the base unit, the drive is controlled by an electronic controller (not shown), which preferably comprises a computer. As the drive rotates the carousel the position of the carousel is detected by the encoder 60 and fed back to the controller. The controller thereby is provided with information about which receiving positions of the carousel have delivered vials to the exit. The container feeder 20 can be detached from the base unit 70, for example to enable it to be connected to a fresh package of vials and/or for maintenance.

Figure 8:
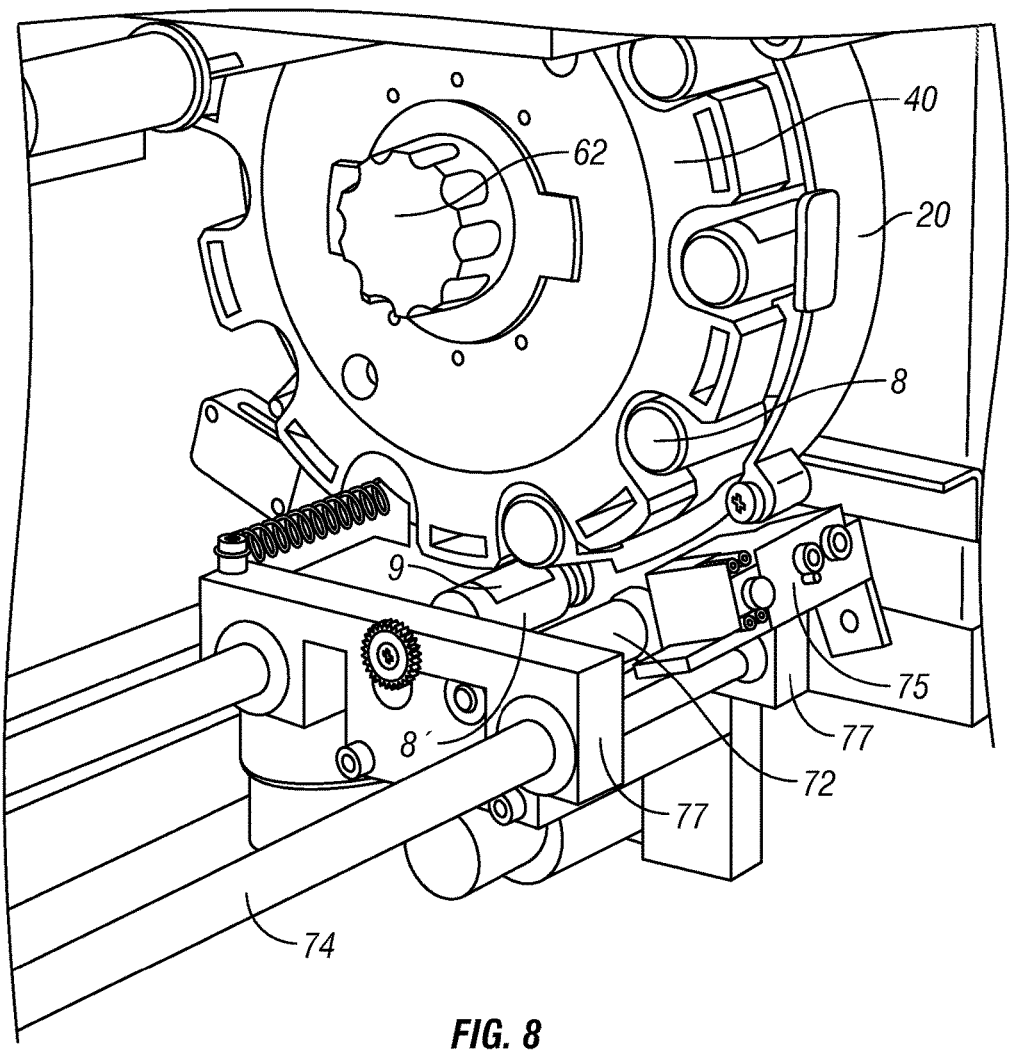
FIG. 8 shows a cut away view of a container feeder in accordance with the invention in position in a base unit as shown in FIG. 7 in which the cut away shows vials being fed from their package by the container feeder and exiting onto rollers for orienting and preparing for pick up by a transport assembly on a robotic arm.

Referring to FIG. 8, there is shown a cut away view showing detail of a container feeder 20 in accordance with the invention in position in the base unit 70. The cut away shows the feeder 20 with one half of its casing 21 removed so that the carousel 40 is visible inside. The carousel 40 has an integral toothed lug 62 that can be driven, i.e. rotated, through engagement with the drive on the base unit 70. As the carousel is rotated in this way, vials 8 are fed one at time from their package 2 into the cut out receiving positions in the carousel and fed by the carousel to the feeder exit 27 whereupon the vials drop one at time from the feeder.

In the embodiment of workflow shown in this example for a printing unit, the vials exit the feeder 20 onto a pair of rollers 72 (only one of which is visible in the drawing) for orienting and preparing the vial 8' for pick up by a transport slide assembly on a robotic arm 74. Optionally the rollers 72 can rotate the vial 8' until a correct orientation is achieved, e.g. until an optical sensor 75 locates an edge (e.g. an edge of a label or writing area 9 on the vial). When the vial 8' is correctly oriented, a pair of robotic jaws 77, which are part of the transport slide on the robotic arm, close onto the oriented vial holding it in position. The transport slide is then driven to the printing unit 80.

Figure 9A:
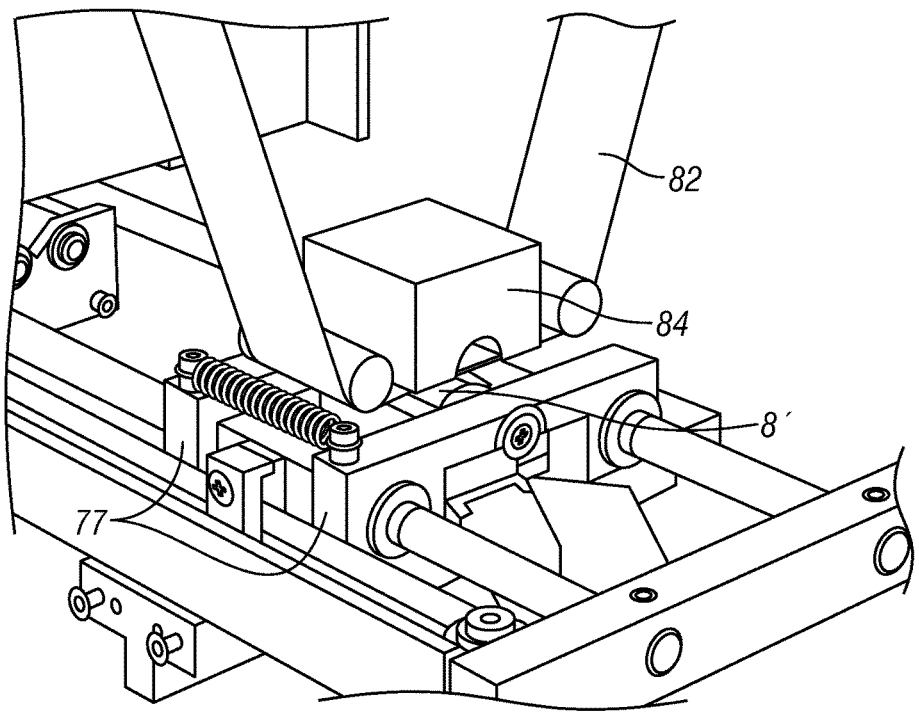
FIGS. 9A and 9B show a transport assembly on a robotic arm that has moved a selected vial to a printing station, wherein a heated printing block is shown in its raised (non-contact) position (FIG. 9A) and its lowered (contact) position (FIG. 9B).
Figure 9B:
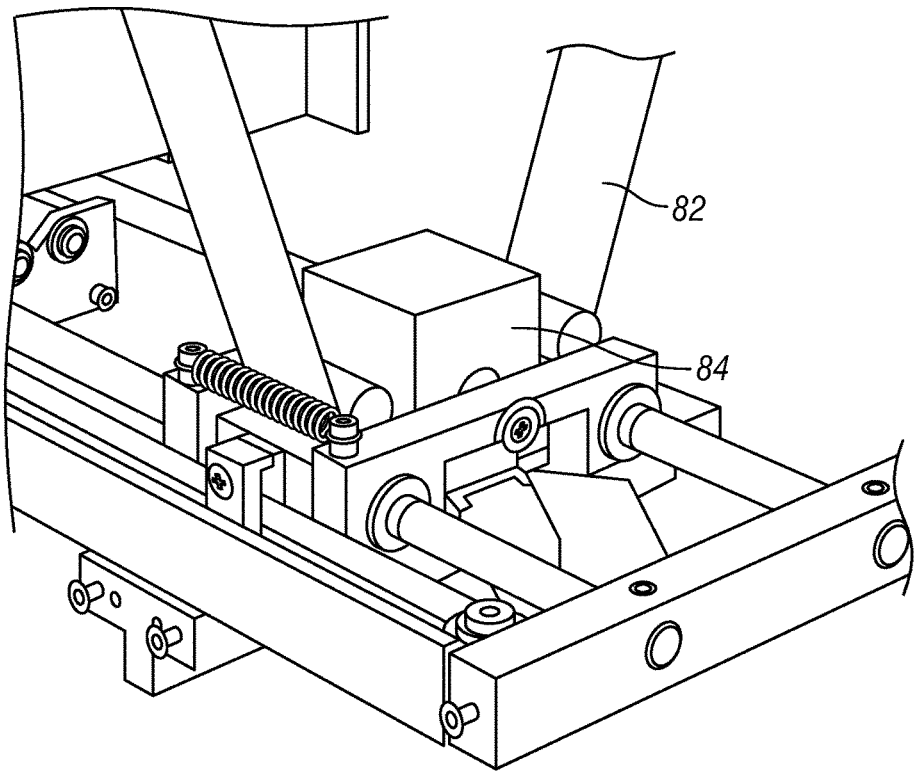

FIG. 9A shows the vial 8' after it has been transferred to the printing unit 80. A dye sublimation type printing process is preferably employed to mark the vials, for example as described in WO 2013/059568. A printed tape 82 carrying dye is moved, e.g. by rollers, to the correct position in proximity to the vial 8' and under a heated block 84. The block 84 is pressed down as shown in FIG. 9B thereby sandwiching the tape between the block and the vial. The dye from the tape vapourises and transfers to the writing surface (label or marking area) of the vial. After printing the block is then moved up and away from the printed vial. In this way, vials may be printed with any suitable label or legend. A tape magazine that slides into position can be employed to make loading of the tape into the device easy for a user.

Figure 10A:
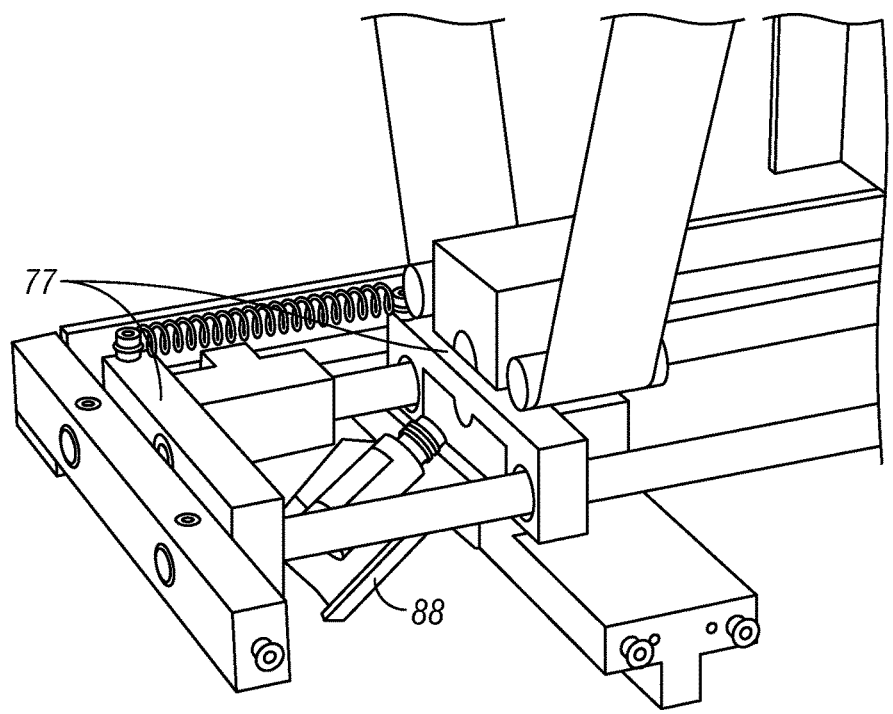
FIGS. 10A and 10B show the transport assembly of FIGS. 9A and 9B ejecting a printed vial into a collection system.
Figure 10B:
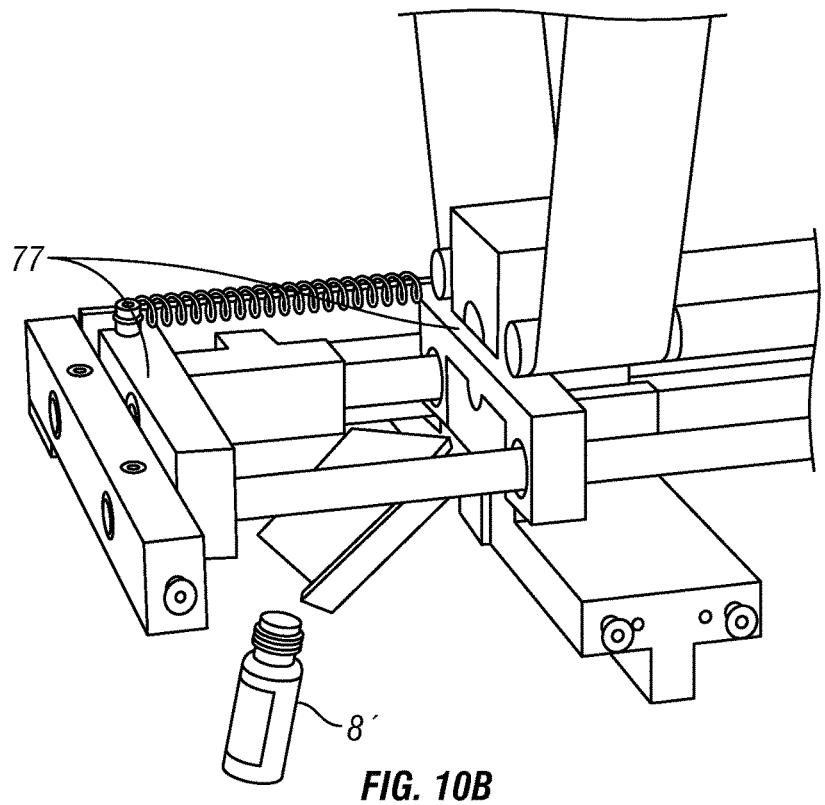

Finally, as shown in FIGS. 10A and 10B, at least one transport assembly jaw 77 opens so that the printed vial 8' is ejected and guided by chute 88 into a collection system or collection point (not shown) for the user.

The workflow may optionally incorporate a broken vial filter. For example, if a vial is broken during the transfer process to the printing unit 80, the robotic jaws 77 will no longer be able to grip it properly as they will be prevented from closing by more than enough to grip the vial. As the vial is moved by the jaws it will pass over a filtering station where the broken vial will drop down under gravity. The filter station could also be used to reject vials that fail a scan or test before they are moved to the printing unit.

It will be appreciated that instead of one container feeder being interfaced to a printing unit as shown in the accompanying Figure, two or more container feeders could be used with one printing unit, e.g. with appropriate coordination of transferring of vials to the printing unit. For example, a vial from one feeder could be being prepared for printing (e.g. vial alignment and transfer) whilst a vial from another feeder is being printed. Thus, multiple feeders could provide increased throughput. For applications and markets where throughput is less important a single feeder could be used.

In the field of chromatography, the majority of analysis is carried out using 12 mm×32 mm glass autosampler vials. These vials are of cylindrical form and are usually supplied in bulk packs or trays of usually approximately 100 units. The transfer of these vials from their delivery packaging into the chromatography workflow is currently a manual process. Even where the workflow involves the processing of samples, liquid transfer and analysis being carried out on automated instruments such as autosamplers, the transfer from the packaging to the autosampler unit is still manual. Manual transfer during this stage can introduce quantitative errors due to sample loss, damage to the vials and contamination of the sample. The feed device in accordance with the present invention, however, enables a fully automated process thereby reducing the aforementioned problems. Laboratory containers such as vials can be transferred directly from their packaging to an automated instrument without any manually handling The present invention is not limited to the one instrument illustrated above, i.e. comprising a printing unit, but may be used with little modification to feed individual vials into a variety of collection formats, herein termed receivers. This can allow direct manipulation on a variety of devices. Several examples of receivers for the vials will now be described.

1. Autosampler trays/Compound storage:

Most instruments can use SBS footprint trays or plates holding, e.g. between 40 and 50 vials. The feeder according to the invention may be used to automatically direct vials into such plates without manual intervention.

2. Automated crimping:

The use of electronic and pneumatic crimping instruments has removed the need for manual force being needed to correctly close the crimps on vials but in most cases the vials are still manually introduced to the crimper jaws. For many years the integration of a vial feed mechanism and a crimper has been found only in large scale pharmaceutical packaging, not in medium or small capacity laboratory applications.

3. Automated assembly of screw thread vials and caps.

4. Automated weighing, e.g. tare weighing.

Advantages of the present invention reside in a lack of manual intervention, an increased cleanliness, a reduction in breakage and handling errors, a reduction in vial wastage and an integration of workflow.

Figure 11:
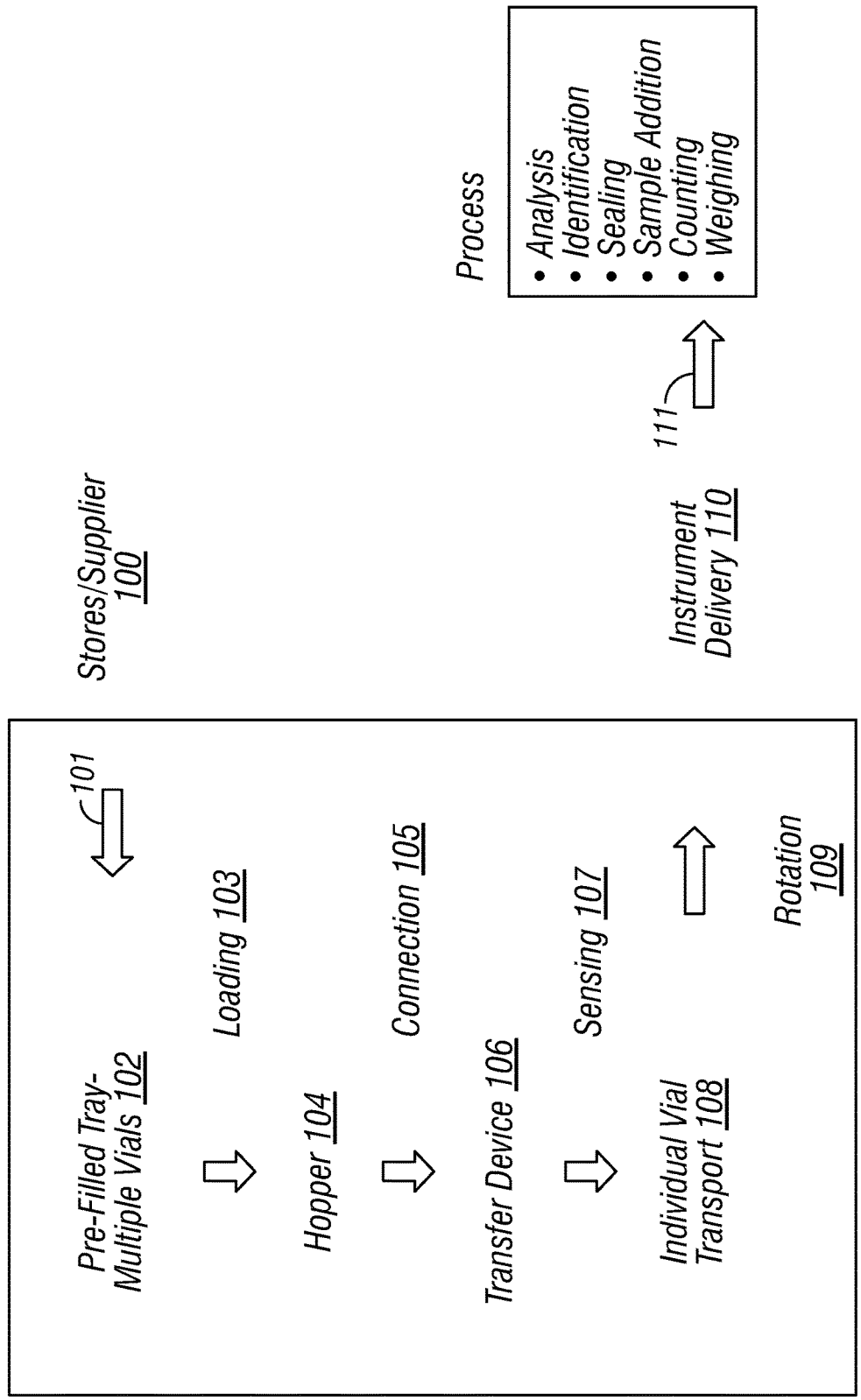
FIG. 11 shows a workflow incorporating an operation of the present invention.

From the specific embodiments above, a generalised or high-level workflow incorporating operation of the present invention is apparent. Such a generalised workflow is illustrated in FIG. 11. Vials packaged by a supplier 100 and transported (step 101) in their package eventually arrive at the user in a pre-filled tray or array of multiple vials 102. The array of vials are loaded (step 103) in a hopper 104, which may comprise the packaging and/or a separate carrier as described above. The hopper is connected (step 105) to the vial transfer device or feeder 106. The vial transfer device senses the collection of the vials (step 107) and provides individual vial transport 108. Operation such as rotation of the transfer device (step 109) enables delivery of the vials to an instrument or receiver 110. The vials may then be processed (step 111) according to the type of instrument or receiver. For example, the process may comprise one or more of: analysis, identification, sealing, sample addition, counting and weighing 112.

The foregoing described embodiments are merely examples of devices according to the invention. It should be understood that various modifications may be made to the shown embodiments whilst still falling within the scope of the invention.

As used herein, including in the claims, unless the context indicates otherwise, singular forms of the terms herein are to be construed as including the plural form and vice versa. For instance, unless the context indicates otherwise, a singular reference, such as "a" or "an" means "one or more".

Throughout the description and claims of this specification, the words "comprise", "including", "having" and "contain" and variations of the words, for example "comprising" and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example", "e.g." and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

What is claimed is:

1. A laboratory vial transfer device for automatically transferring laboratory vials,
   a transport package having an openable end;
   a plurality of laboratory vials contained within the transport package;
   a carrier into which is inserted the transport package;
   a vial feeder configured to receive the transport package after the openable end of the package has been opened, so as to feed vials directly from the open package without manual contact,
   wherein the vial feeder comprises:
      a casing defining a receiving space to receive at least the opened end of the package and the casing further defining an exit aperture that is opposite the receiving space; and
      a rotatable carousel disposed inside the casing between the receiving space and the exit aperture, and having a plurality of vial receiving positions located along a periphery of the carousel each for receiving a single vial and adapted to collect the vials from the opened package into respective vial receiving positions upon operation of the carousel, and
   wherein when the vial feeder is operated the vial receiving positions move through the receiving space and adjacent to the open end of the package as the carousel is rotated, thereby to receive vials from the open package directly into respective vial receiving positions on the carousel and to transport the received vials within the casing between the receiving space and the exit aperture as the carousel is rotated further, and
   wherein the carrier has one or more fasteners to attach the carrier to the vial feeder;
   wherein the carousel is operable to feed the vials from their respective vial receiving positions to an exit position via the exit aperture,
   and wherein the transport package is configured to be disconnected from the vial feeder subsequent to transferring the laboratory vials therefrom.

2. The laboratory vial transfer device as claimed in claim 1 wherein the vial feeder has a rectangular receiving space to receive at least the opened end of the package.

3. The laboratory vial transfer device as claimed in claim 1 wherein the vial feeder has one or more fasteners to attach the vial feeder to the package.

4. The laboratory vial transfer device as claimed in claim 3 wherein the package has one or more recesses to receive the one or more fasteners.

5. The laboratory vial transfer device as claimed in claim 1 wherein the vials are glass vials.

6. The laboratory vial transfer device as claimed in claim 1 wherein the carousel is adapted to collect the laboratory vials singly into respective vial receiving positions on the carousel and operable to deliver the vials one at a time from their respective vial receiving positions to the exit position.

7. The laboratory vial transfer device as claimed in claim 1 wherein the carousel has cut out portions in an outer edge of the carousel, the cut out portions forming the vial receiving positions.

8. The laboratory vial transfer device as claimed in claim 1 further comprising a position encoder to detect a position of the carousel as the carousel rotates.

9. The laboratory vial transfer device as claimed in claim 1 comprising a base unit configured to receive the vial feeder such that the vial feeder supports the package vertically with the open end of the package down and with the vial feeder positioned below and aligned with the open end of the package, the base unit comprising a drive.

10. The laboratory vial transfer device as claimed in claim 1 wherein the vial receiving positions are circumferentially spaced about the periphery of the carousel, one relative to another, such that during use at least two of the vial receiving positions are disposed within the receiving space and facing the open end of the package at all times.

11. The laboratory vial transfer device as claimed in claim 9 further comprising a lock on the carousel to prevent rotation of the carousel when the carousel is disconnected from the drive on the base unit.

12. The laboratory vial transfer device as claimed in claim 9 wherein a robotic system is provided on the base unit for transferring vials to a receiver after the vials have reached the exit position.

13. The laboratory vial transfer device as claimed in claim 9 wherein the vial feeder is configured to receive vials from the open package under gravity.

14. A method of automatically transferring laboratory vials from a transport package containing a plurality of said vials, comprising:
   providing a carrier into which is inserted the transport package, wherein the carrier has one or more fasteners to attach to the carrier to the vial feeder;
   opening the transport package to provide an open end of the transport package;

connecting the open end to a vial feeder configured to connect to the fasteners on the carrier after the transport package has been opened, the vial feeder comprising a casing defining a receiving space configured to receive the open end of the package and an exit aperture formed in a portion of the casing that is opposite the receiving space, the vial feeder further comprising a rotatable carousel disposed within the casing between the receiving space and the exit aperture, the rotatable carousel having a plurality of vial receiving positions located along a periphery thereof, each vial receiving position for receiving a single vial and adapted to collect the vials from the opened package into respective vial receiving positions upon operation of the carousel;

subsequent to connecting the vial feeder to the carrier, inserting the vial feeder into a base unit such that the rotatable carousel engages a drive of the base unit and the package is held vertically with the open end of the package down and the vial feeder positioned below and aligned with the open end of the package; and operating the drive when engaged with the rotatable carousel, so as to cause the carousel to move the vial receiving positions through the receiving space and adjacent to the open end of the package so as to feed vials directly from the package without manual contact, whereby the carousel feeds the vials from their respective vial receiving positions to an exit position via the exit aperture.

15. The method as claimed in claim 14 wherein the step of inserting the vial feeder comprises aligning lugs extending from a center of one side of the carousel with the drive of the base unit.

16. The laboratory vial transfer device as claimed in claim 9 comprising lugs projecting from the center of one side of the carousel and through an aperture in the casing for engaging a drive of the base unit so as to support rotational driving of the carousel.

* * * * *